United States Patent [19]

Masurekar et al.

[11] Patent Number: 5,578,581
[45] Date of Patent: Nov. 26, 1996

[54] ACTIVE AVERMECTIN ANALOGUE

[75] Inventors: Prakash S. Masurekar, Warren; Wesley L. Shoop, Somerville; Michael A. Wallace, Lebanon; Richard L. Monaghan, Somerset, all of N.J.

[73] Assignee: Merck & Co., Inc., Rahway, N.J.

[21] Appl. No.: 233,489

[22] Filed: Apr. 26, 1994

[51] Int. Cl.$^6$ ............... A61K 31/70; C07H 17/08
[52] U.S. Cl. ............................ 514/30; 536/7.1
[58] Field of Search ................. 514/30; 536/7.1

[56] References Cited

U.S. PATENT DOCUMENTS

| | | | |
|---|---|---|---|
| 4,171,314 | 10/1979 | Chabala et al. | 549/264 |
| 4,206,205 | 6/1980 | Mrozik et al. | 514/30 |
| 4,310,519 | 1/1982 | Albers-Schonberg et al. | 514/30 |
| 4,427,663 | 1/1984 | Mrozik | 514/30 |
| 4,457,920 | 7/1984 | Mrozik | 514/30 |
| 4,874,749 | 10/1989 | Mrozik | 514/30 |
| 5,015,630 | 5/1991 | Fisher et al. | 514/30 |
| 5,023,241 | 6/1991 | Linn et al. | 514/30 |
| 5,212,322 | 5/1993 | Okazaki et al. | 549/265 |

OTHER PUBLICATIONS

E. W. Hafner, et al., The Journal of Antibiotics, vol. 44, No. 3, pp. 349–356, Mar. 1991.

*Primary Examiner*—John Kight
*Assistant Examiner*—Howard C. Lee
*Attorney, Agent, or Firm*—Robert J. North; Melvin Winokur

[57] ABSTRACT

An active avermectin analogue which can be produced by directed biosynthesis is described. The compound, named 26-R-Avermectin $B_1a$, is active in the Haemonchus egg to L3 assay and has the following structure:

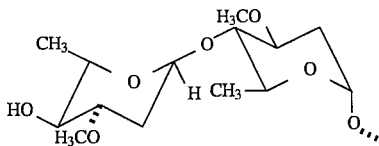

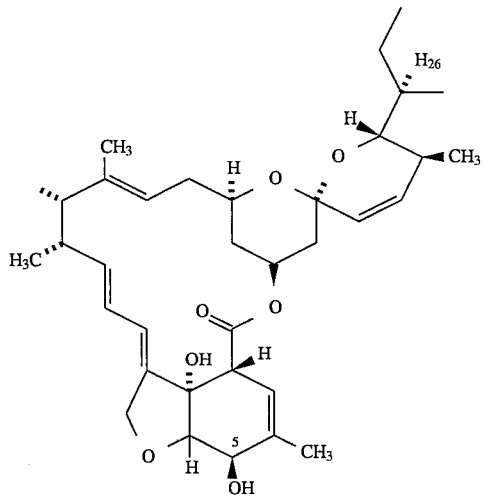

6 Claims, 2 Drawing Sheets

ACTIVE AVERMECTIN ANALOGUE

BACKGROUND OF THE INVENTION

1. Field of the Invention

The present invention relates to an active avermectin analogue, 26-epi-avermectin $B_1a$, which is active as an antiparasitic for use in treating animals and pets for parasitic infections.

2. Brief Disclosures in the Art

Avermectins are a well known class of antiparasitic agents which are effective in treating a variety of animals and pets to combat a variety of parasitic infections.

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519 and 4,429,042 and are incorporated herein by reference. They describe the general class of avermectins and their broad spectrum activity against insect pests, acarid, free-living nematodes and parasites affecting animals. They particularly exhibit efficacy against the important parasitic worms or arthropods afflicting livestock, domesticated animals or humans.

The avermectin compounds are a series of macrolides, each of which is substituted thereon at the 13-position with a 4'-(α-L-oleandrosyl)-α-L-oleandrose group. Avermectin compounds and the specific derivative thereof of this invention, have a very high degree of anthelmintic and antiparasitic activity.

DESCRIPTION OF THE PRIOR ART

The avermectin series of compounds from which the derivatives of the invention are derived have the following structure:

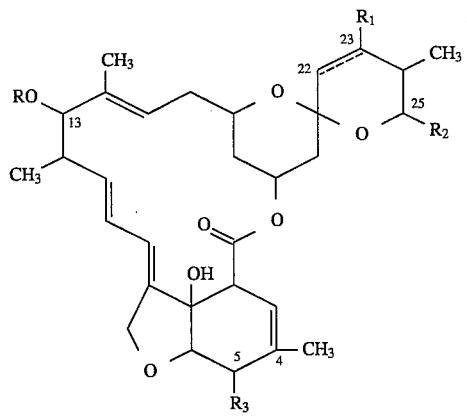

I wherein

R is the 4'-(α-l-oleandrosyl)-α-l-oleandrose group of the structure:

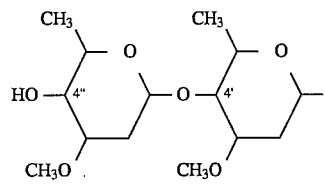

II and wherein the broken line indicates a single or a double bond;

$R_1$ is hydroxy and is present only when said broken line indicates a single bond;

$R_2$ is iso-propyl or sec-butyl; and $R_3$ is methoxy or hydroxy.

There are eight different major avermectin natural product compounds and they are given the designations A1a, A1b, A2a, A2b, B1a, B1b, B2a and B2b based upon the structure of the individual compounds.

In the foregoing structural formula, the individual avermectin compounds are as set forth below. (The R group is 4'-(α-L-oleandrosyl)-α-L-oleandrose):

|     | $R_1$              | $R_2$      | $R_3$    |
|-----|--------------------|------------|----------|
| A1a | (22,23-Double Bond) | sec-butyl  | —OCH₃   |
| A1b | (22,23-Double Bond) | iso-propyl | —OCH₃   |
| A2a | —OH                | sec-butyl  | —OCH₃   |
| A2b | —OH                | iso-propyl | —OCH₃   |
| B1a | (22,23-Double Bond) | sec-butyl  | —OH     |
| B1b | (22,23-Double Bond) | iso-propyl | —OH     |
| B2a | —OH                | sec-butyl  | —OH     |
| B2b | —OH                | iso-propyl | —OH     |

The avermectin compounds are generally isolated as mixtures of homologous "a" and "b" components. Such compounds differ only in the nature of the $R_2$ substituent and the minor structural difference has been found to have very little effect on the isolation procedures, chemical reactivity and biological activity of such compounds.

In the isolation of the avermectin compounds from the fermentation broth, which serve as starting materials for the instant processes, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25-position. This difference, of course, does not interfere with any of the instant reactions. In particular it may not be necessary to separate the "b" component from the related "a" component. Separation of these closely related compounds is often not practiced since the "b" compound often is present only in a small amount, and the structural difference has negligible effect on the reaction processes and biological activities.

In particular it has been found that the starting materials for the compounds of this invention are conveniently prepared in a ratio of about 80% to 95% avermectin B1a or A1a and less than 20% avermectin B1b or A1b. Thus the preferred composition of this invention is one which contains not less than 80% of the "a" component and not more than 20% of the "b" component.

The Journal of Antibiotics, Vol. 44, No. 3, p. 349–356 by E. W. Hofner et al. discloses a novel avermectin produced from "unnatural" R(–) isomer of 2-methylbutyric acid. However, there is no structure presented nor a description of any biological activity. The unexpectedly superior properties of the instant compound are not suggested.

There is a constant search for avermectin analogues exhibiting greater efficacy against the parasites which normally infect animals and important livestock.

SUMMARY OF THE INVENTION

Figure 1:
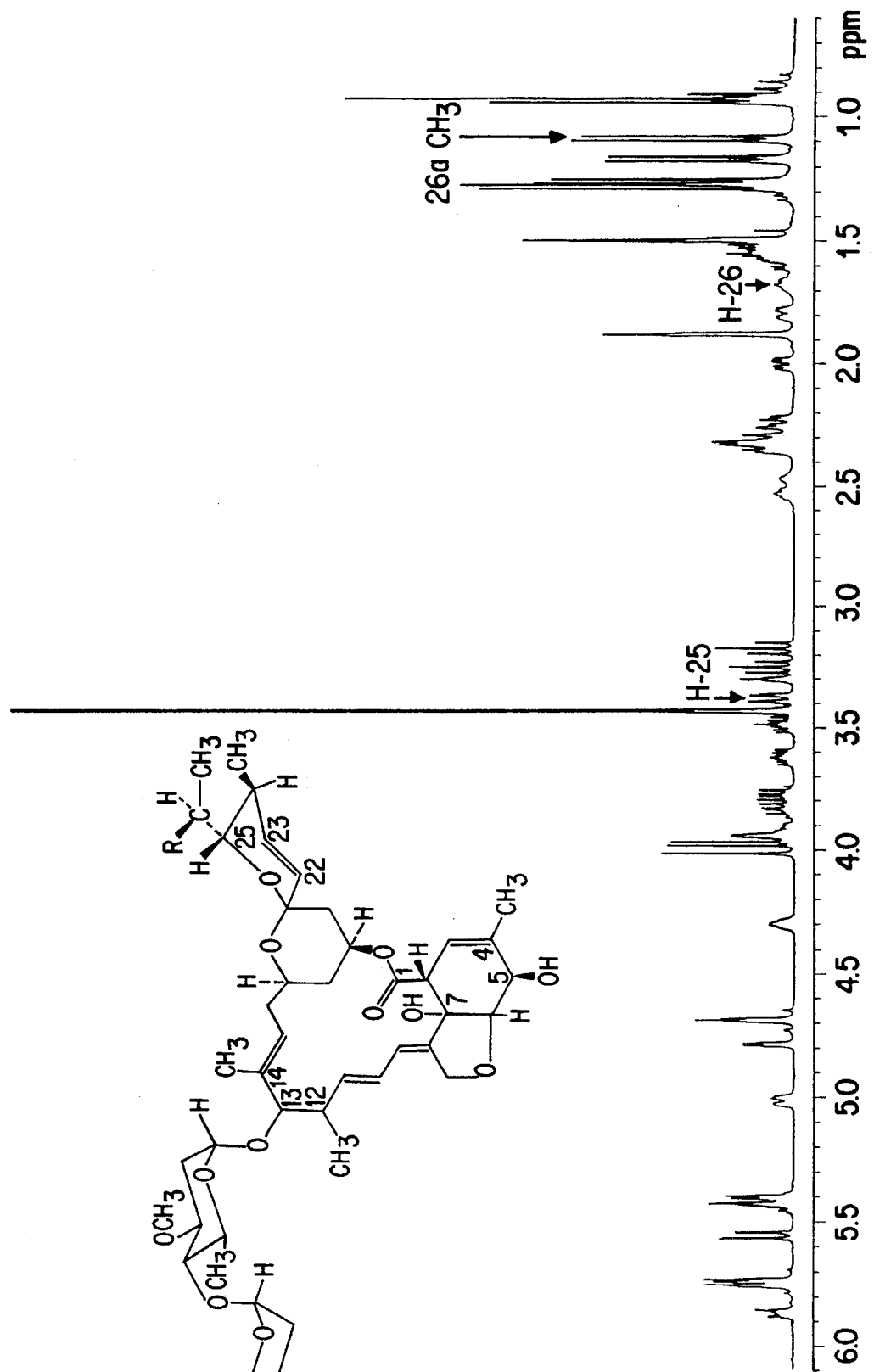
FIG. 1 is an $^1H$ nuclear magnetic resonance (NMR) spectrum taken at 400 MHz of 26-epi-avermectin $B_1a$ in CDCl$_3$, and also illustrates the assigned molecular structure of the compound.

We have discovered that the avermectin analogue, 26-epi-avermectin B$_1$a, containing a 26-epi hydrogen atom and having the structure illustrated below, is unexpectedly very active in in vitro parasitic assays as compared to the normal isomer of ivermectin B$_1$a.

By this invention there is provided a novel method for the treatment of animals suffering from parasitic conditions comprising the step of administering 26-epi avermectin B$_1$a of the structure:

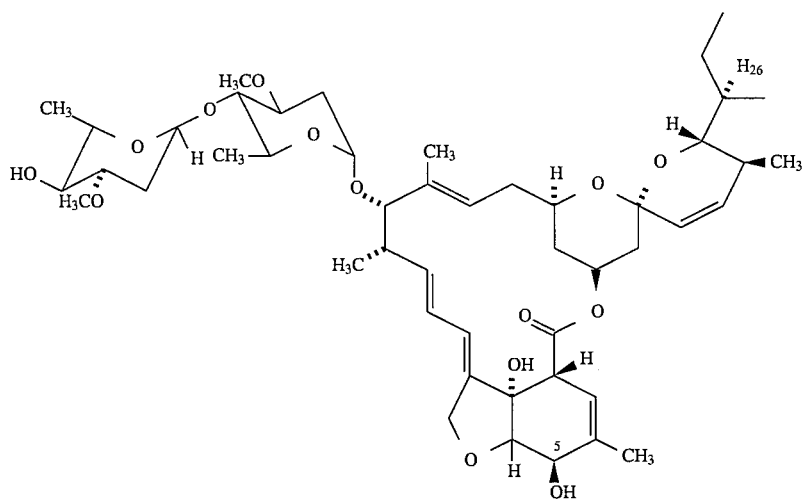

26-epi-Avermectin B$_1$a

Avermectin B$_1$a (normally produced) by contrast has the same structure as above except the 26-hydrogen is written as a solid wedged line to indicate a beta configuration above the plane of the paper. Ivermectin has the same structure as Avermectin B$_1$a except that the oxane ring to which the 26-sec butyl group is attached does not have the 22,23-double bond.

Also provided by this invention is a pharmaceutical composition containing a therapeutically effective amount of the above-described compound in a pharmaceutically acceptable excipient.

The 26-epi compound can be produced through directed biosynthesis by selectively feeding chiral 2-R-methylbutyric acid to increase the yield of desired product to the avermectin fermentation as a nutrient in place of the regular nutrient 2-S-methylbutyric acid. Smaller amounts of the 5-methoxy analog are also provided in the fermentation which is also an active anti-parasitic agent.

The chiral R-2-methylbutyric acid is added to a fermentation medium containing *Streptomyces avermitilis*, a carbon source and a nitrogen source at pH of about 7, and a temperature of about 25–30 degrees C. and allowing the fermentation to proceed for a sufficient time to produce the compound. Preferably said *Streptomyces avermitilis* is ATCC No. 31271.

DESCRIPTION OF THE INVENTION

The method of this invention involves the compound having the following structural formula:

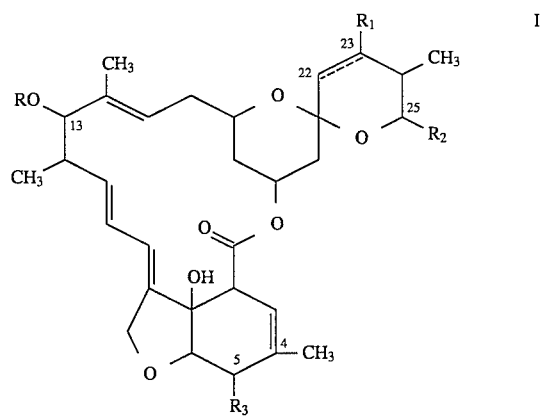

wherein

R is the 4'-(α-l-oleandrosyl)-α-l-oleandrose group of the structure:

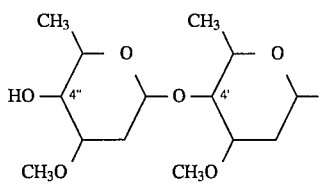

and wherein
the broken line indicates a single or a double bond;
$R_1$ is hydroxy and is present only when said broken line indicates a single bond;
$R_2$ is 26-epi-sec-butyl; and
$R_3$ is methoxy or hydroxy.
Particularly preferred is the compound of the structure:

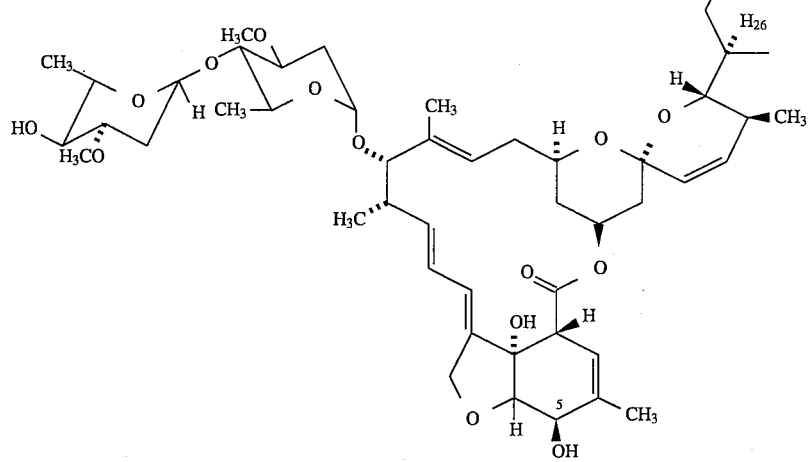

26-epi-Avermectin B$_1$a

DISCUSSION OF UTILITY

The method of this invention includes the above compound which has significant parasiticidal activity as an anthelmintic, ectoparasiticide, insecticide and acaricide, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in death of the infected host. The avermectin compound described herein has unexpectedly high activity against these parasites, and in addition is also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compound is also useful against parasites which infect humans. The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. This compound is also of value against arthropods parasitizing man, biting insects and other dipterous pests causing annoyance to man.

The compound is also active against household pests such as the cockroach, Blatella sp.,clothes moth, Tineola sp., carpet beetle, Attagenus sp., and the housefly *Musca domestica.*

The compound is also useful against insect pests of stored grains such as Tribolium sp., Tenebrio sp. and of agricultural plants such as 2 spider mites, (Tetranychus sp.), aphids, (Acyrthiosiphon sp.); against migratory orthopterans such as locusts and immature stages of insects living on plant tissue. The compound is useful as a nematocide for the control of soil nematodes and plant parasites such as Meloidogyne spp. which may be of importance in agriculture. The compound is active against other plant pests such as the southern army worm and Mexican bean beetle larvae.

This compound may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivative in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alteratively, the antiparasitic compound of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound is dissolved or suspended in the parenteral formulation for administration; such formulations generally contain from 0.005 to 5% by weight of the active compound.

Although the antiparasitic agent of this invention finds its primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. It is also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our compound by the oral administration of from about 0.001 to 10 mg per kg of animal body weight, such total dose being given at one time or in divided doses over a relatively short period of time such as 1–5 days. With the disclosed compound of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compound described herein is administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compound described in this invention is usually fed at concentrations of between 0.00001 to 0.002% in the feed in order to achieve the desired antiparasitic result.

The avermectin compound of this invention is also useful in combatting agricultural pests that inflict damage upon crops while they are growing or while in storage. The compound is applied using known techniques as sprays, dusts, emulsions and the like, to the growing or stored crops to effect protection from such agricultural pests.

The following examples are provided in order that this invention might be more fully understood; they are not to be construed as limitative of the invention.

EXAMPLE 1

The following procedure was followed to prepare R-26-epi-avermectin B1a.

Culture: MA 4848 (Species, ATCC No. 31271
(U.S. Pat. No. 4,412,991))

A frozen vial of MA 4848 was thawed at room temperature and one ml of it was used to inoculate a seed flask.

Media

| Seed medium: BaSa | |
|---|---|
| | g/l |
| HyCase | 20 |
| Dextrose | 20 |
| Yeast Extract | 20 |
| $KNO_3$ | 2 |
| $FeSO_4 \cdot 7H_2O$ | 25 mg |
| NaCl | 500 mg |
| $MgSO_4 \cdot 7H_2O$ | 500 mg |
| $MnSO_4 \cdot H_2O$ | 5 mg |
| $ZnSO_4 \cdot 7H_2O$ | 10 mg |
| $CaCl_2 \cdot 2H_2O$ | 20 mg |

Medium pH was adjusted to 7.0 with NaOH. Twenty five ml of the medium were dispensed into 250 ml baffled, Erlenmeyer flasks and autoclaved for 20 minutes at 121° C.

| Production medium: LI | |
|---|---|
| | g/l |
| Cerelose | 45 |
| Peptonized Milk | 24 |
| Ardamine PH | 2.5 |

Medium pH was adjusted to 7.0 with NaOH. Forty ml of the medium were dispensed into 250 ml unbaffled Erlenmeyer flasks and autoclaved for 20 minutes at 121° C.

Fermentation

Seed: Single stage seed grown for 16 hours at 28° C. and 220 RPM was used.
Production: Flasks were shaken for 10 days at 28° C. and 220 RPM.

Precursor Addition

A solution containing 20 mg chiral R-2-methylbutyric acid/ml (Chem Abs. Reg. No. 33231-50-8) was adjusted to pH 7.0 and filter sterilized. This was added to the fermentation flasks at 72 hours and every 24 hours thereafter from day 3 to day 7 in one addition of 4 mg/flask/day.

Harvest

At the end of 10 days the flasks were pooled and two 5 ml aliquots taken for assay. Two flasks with no addition (control) were also sampled. To these four samples were added four volumes of methanol to give a final methanol concentration of 80%. These were then shaken on a reciprocating shaker for 30 minutes. The samples were clarified by centrifuging twice, first at 1800 RPM in a Beckman TJ-6 for 15 minutes and then in a high speed microfuge for 5 minutes. The clarified methanol extract was then assayed for antiparasitic activity as described in Example 3.

EXAMPLE 2

Isolation of 26-epi Avermectin $B_1a$

The crude avermectin mixture was isolated from the fermentation broth described above in Example 1 by centrifugation, decantation of the aqueous medium, and extraction of the cellular mass with methanol. Following removal of the lipids and other cellular impurities by passing through a silica gel pad, the crude mixture was crystallized from ethanol/hexane, and the isolated solids purified by reverse phase HPLC (Zorbaz M9 C8-RX, 40% A to 55% A over 1.0 h, A=$CH_3CN$, B=$H_2O$, 6 mL/min) to afford pure avermectin $B_1a$. Analysis using a Hypercarb graphitized column (30% $CHCl_3$/70% $CH_3CN$/10% IPA to 50% $CHCl_3$/50% $CH_3CN$/10% IPA over 20 min) indicated the mixture contained 9% of the 26-epi isomer.

The 26-epi $B_1a$ isomer was separated from avermectin $B_1a$ by preparative HPLC using a 1 inch Hypercarb column (gradient 0 to 29% A over 60 min: A=$CHCl_3$/10% IPA, B=$CH_3CN$/10% IPA). This purification procedure afforded 18 mg of pure 26-epi Avermectin $B_1a$. The 26-epi $B_1a$ was later repurified by preparative HPLC (Zorbax RX-C8, 40% A step gradient to 60% A over 60 min: A=$CH_3CN$, B=$H_2O$) to afford 15 mg of pure 26-epi Avermectin $B_1a$.

Figure 2:
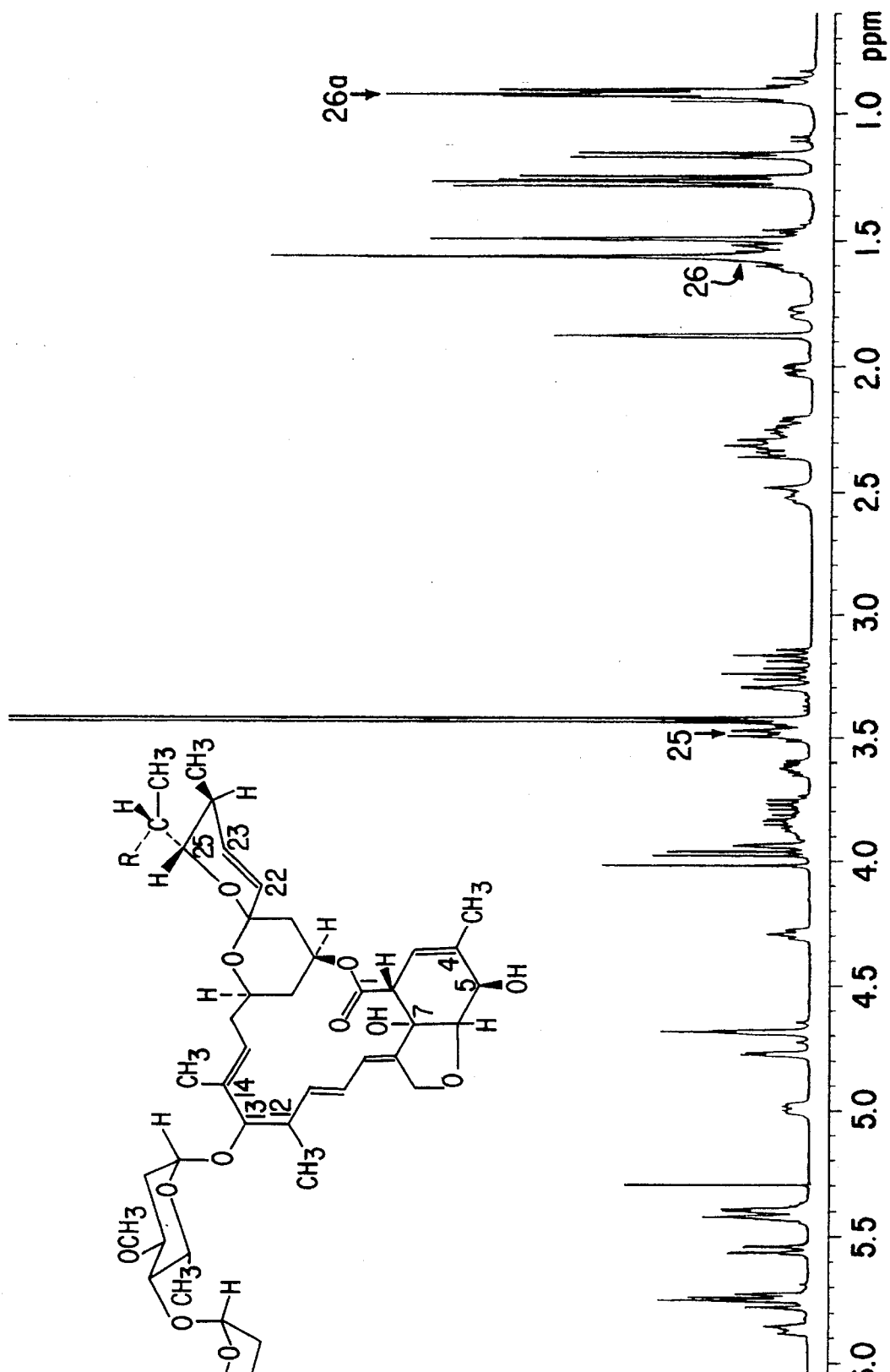
FIG. 2 is an $^1$H nuclear magnetic resonance (NMR) spectrum taken at 400 MHz of avermectin B$_1$a in CDCl$_3$ and also illustrates the assigned molecular structure of the compound.

The 400 MHz nuclear magnetic resonance spectrum in $CDCl_3$ (FIG. 1) of the obtained 26-epi isomer showed a distinct spectral difference from that of the normal $B_1a$ isomer (FIG. 2). The 26-epi $B_1a$ showed a downfield displacement of the 26-alpha methyl/protons (0.15 ppm) and the 26-H (0.1 ppm) and an upfield shift (0.1 mm) of the 25-H, all versus the normal $B_1a$ isomer.

The mass spectrum was obtained using a SCIEX API III mass spectrometer using soft ionization ion spray, showing a molecular ion of 872 (the 891 value observed includes $C^{13}$ and $NH_4^+$ ion mass units) for both the 26-epi $B_1a$ and the normal $B_1a$ compounds. Further mass spectra of each molecular ion peak showed that the daughter peaks and splitting patterns were substantially identical. In summary, the NMR spectra of the two compouds, differ, but the mass spectra of each are identical which is consistent with the presence of two stereoisomers. The NMR and mass spectral data is consistent with the assigned molecular structure for 26-epi $B_1a$ shown in FIG. 1.

EXAMPLE 3

Haemonchus Egg To L3 Assay (Hel) Summary Results

Summaries are presented in the following table of three Haemonchus Egg to L3 Assays in which ivermectin and 26-epi Avermectin $B_1a$ were tested.

The "HEL" assay is an acronym for Haemonchus egg to larva assay. *Haemonchus contortus* is a sheep parasite that is cultured in vitro. This is carded out by collecting eggs from the feces of an experimentally infected sheep and then placing them in microwell plates with water. Various concentrations of drug are added to the water, the eggs then hatch, and proceed to develop through two molts over the course of 5 days in the presence of drug. At the end of the 5 days, the number of parasites that have advanced to the L3 stage from the control, untreated wells are compared to those that have been given the various concentrations of drug.

The following symbols are used in the table. An AD (active, dead) score means eggs hatched but larvae failed to develop and died. An AM (active, molt inhibition) score described activity in which eggs hatch, most larvae survive, but the majority fail to reach the L3 stage. An I score means inactive, where virtually all larvae reach the L3 stage appear normal.

The data showed 26-epi avermectin $B_1a$ had activity to 0.0001 micrograms/ml, approximately 10-fold better than ivermectin.

| | ASSAY RESULTS | | | |
|---|---|---|---|---|
| | Micrograms/ml 0.01 | Micrograms/ml 0.001 | Micrograms/ml 0.0001 | Micrograms/ml 0.00001 |
| IVERMECTIN | AD | AM | I | I |
| IVERMECTIN | AD | AM | I | I |
| IVERMECTIN | AD | AM | I | I |

-continued

ASSAY RESULTS

|  | Micrograms/ml 0.01 | Micrograms/ml 0.001 | Micrograms/ml 0.0001 | Micrograms/ml 0.00001 |
|---|---|---|---|---|
| IVERMECTIN | AD | I | I | I |
| 26-Epi AVM B1a | AD | AD | AM | I |
| 26-Epi AVM B1a | AD | AD | AM | I |

AD — Active, All Dead
AM — Active, Molt Inhibition
I — Inactive
*Egg Hatch Inhibition

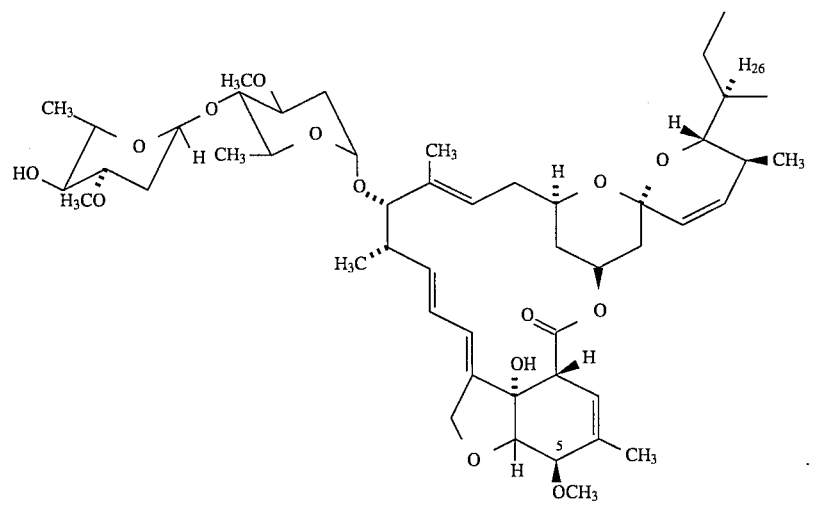

What is claimed is:

1. A method for treating an animal suffering from a parasitic condition which comprises administering a therapeutically effective amount of a compound of the structure:

[Structure I]

wherein

R is the 4'-(α-l-oleandrosyl)-'-l-oleandrose group of the structure:

[Structure II]

and wherein the broken line indicates a single or a double bond;

$R_1$ is hydroxy and is present only when said broken line indicates a single bond;

$R_2$ is 26-epi-sec-butyl; and $R_3$ is methoxy or hydroxy.

2. The method of claim 1 wherein said compound is of the structure:

26-epi-Avermectin B₁a

3. The method of claim 1 wherein said compound is of the structure:

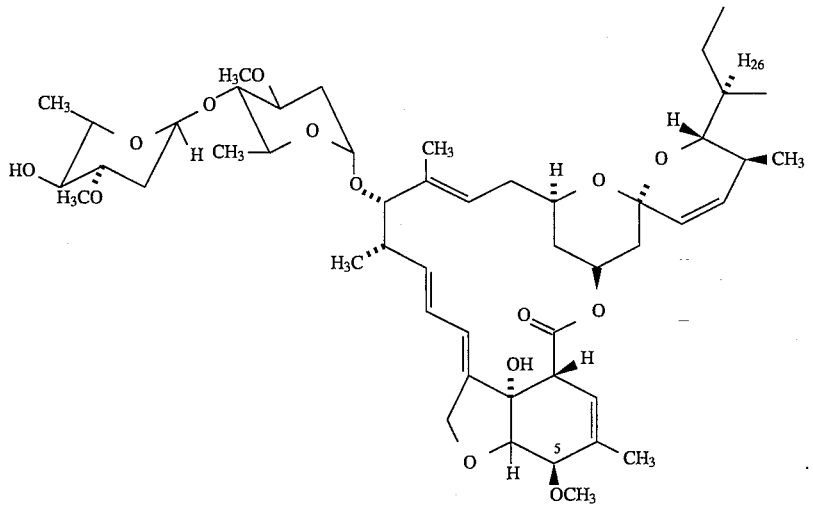

4. A pharmaceutical composition for treatment of animals infected with parasites which comprises a therapeutically effective dosage amount of a compound of the structure defined in claim 1 and a pharmaceutically acceptable carrier.

5. The pharmaceutical composition of claim 4 for treatment of animals infected with parasites which comprises a therapeutically effective dosage amount of a compound of the structure:

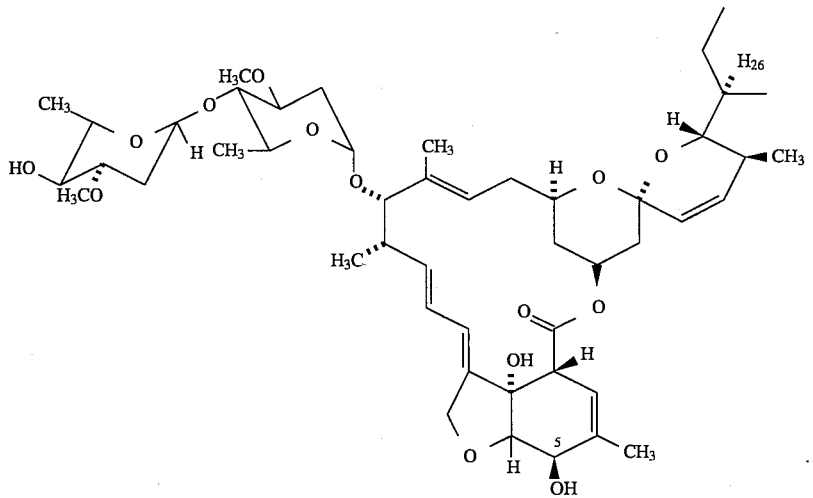

26-epi-Avermectin $B_{1a}$

6. The pharmaceutical composition of claim 4 for treatment of animals infected with parasites which comprises a therapeutically effective dosage amount of a compound of the structure: